(12) United States Patent
Victor

(10) Patent No.: US 10,603,052 B2
(45) Date of Patent: Mar. 31, 2020

(54) BONE CUTTER FOR CREATING HEMISPHERICAL CAVITIES

(71) Applicant: Greatbatch Ltd., Clarence, NY (US)

(72) Inventor: Gary C. Victor, Wheatfield, NY (US)

(73) Assignee: Viant AS&O Holdings LLC, Foxborough, MA (US)

( * ) Notice: Subject to any disclaimer, the term of this patent is extended or adjusted under 35 U.S.C. 154(b) by 1084 days.

(21) Appl. No.: 14/665,897

(22) Filed: Mar. 23, 2015

(65) Prior Publication Data

US 2016/0278792 A1    Sep. 29, 2016

(51) Int. Cl.
*A61B 17/16* (2006.01)
*A61B 17/00* (2006.01)

(52) U.S. Cl.
CPC ...... *A61B 17/1666* (2013.01); *A61B 17/1659* (2013.01); *A61B 2017/00526* (2013.01)

(58) Field of Classification Search
CPC ............ A61B 17/1666; A61B 17/1659; A61B 17/1613; A61B 17/1633; A61B 17/1682; A61B 17/1664; A61B 17/1642
See application file for complete search history.

(56) References Cited

U.S. PATENT DOCUMENTS

| | | | |
|---|---|---|---|
| 4,811,632 A | 3/1989 | Salyer | |
| 7,097,646 B2 | 8/2006 | Schantz | |
| 7,220,264 B1 * | 5/2007 | Hershberger | A61B 17/1666 606/81 |
| 7,608,076 B2 | 10/2009 | Ezzedine | |
| 7,850,692 B2 | 12/2010 | White et al. | |
| 7,896,881 B2 | 3/2011 | Cutshall et al. | |
| 8,096,992 B2 | 1/2012 | Berthusen | |
| 8,435,243 B2 * | 5/2013 | White | A61B 17/1666 606/79 |
| 2007/0225723 A1 * | 9/2007 | Berthusen | A61B 17/1666 606/81 |
| 2011/0152868 A1 | 6/2011 | Kourtis et al. | |
| 2011/0202060 A1 * | 8/2011 | White | A61B 17/1666 606/80 |
| 2013/0204254 A1 * | 8/2013 | Slone | A61B 17/1666 606/81 |
| 2013/0226185 A1 | 8/2013 | Bonutti | |
| 2013/0267957 A1 | 10/2013 | Stamp | |

FOREIGN PATENT DOCUMENTS

GB    2495090    4/2013

* cited by examiner

*Primary Examiner* — Lynnsy M Summitt
*Assistant Examiner* — Tara Rose E Carter
(74) *Attorney, Agent, or Firm* — Steven J. Grossman; Grossman Tucker Perreault & Pfleger PLLC

(57) ABSTRACT

An orthopedic bone cutter for cutting bone and tissue is described. The cutting device comprises a plurality of radially extending struts that form a frame to which a base is connected thereto. Each of the struts that form the frame comprise sidewalls having left and right sidewall portions that are positioned at an angular relationship with respect to a primary strut sidewall portion. A plurality of cutting teeth reside along each of the struts have a tissue cutting surface that is raised above the exterior strut surface. The base of the orthopedic bone cutter may comprise a cross bar or bar and boss interface which secure bone cutter to a drive shaft.

15 Claims, 15 Drawing Sheets

Present Invention

BONE CUTTER FOR CREATING HEMISPHERICAL CAVITIES

TECHNICAL FIELD

This invention relates to the art of instruments used in orthopedic surgery. More specifically, this invention relates to an acetabular reamer for cutting the cotyloid cavity of the acetabulum for the placement of a hip joint prosthetic cup.

BACKGROUND OF THE INVENTION

Bone cutters, such as acetabular reamers, are surgical tools which are used to cut a partial hemispherically-shaped cavity within a bone. In particular, an acetabular reamer is an orthopedic surgical tool used to cut a partial hemispherically-shaped cavity within a pelvic bone for the insertion of a prosthetic cup during an artificial hip joint procedure.

Acetabular reamers must be capable of producing cavities having precise dimensions to ensure the proper positioning of a prosthetic cup within the pelvic bone. As such, traditional reamers, such as those disclosed in U.S. Pat. No. 4,811,632 to Salyer, are constructed having a hemispherical cup-like shape. These prior art reamers are fabricated with a plurality of cutting surfaces that are precisely positioned extending from the curved surface of the curved reamer shell. The hemispherical cup-like body construction provides the reamer with structural rigidity that enables a precise cut. Fabrication of these traditional reamers is often difficult and cost prohibitive. Traditional reamers like that of Salyer require precise positioning of a multitude of cutting surfaces along a curved convex shape of a reamer shell. This requires the use of intricate tooling and expertise. Therefore, because of the high cost of these tools, traditional reamers are often cleaned and sterilized for reuse in multiple surgical procedures.

However, traditional reamers, like Salyer, are often difficult to clean and sterilize. After use, soft tissue embedded in the tool is often difficult to remove. As a result, the surfaces of these reamers may become contaminated with bacteria or micro-organisms which may cause adverse surgical outcomes. Consequently, cutting tools such as those disclosed by Stamp in U.S. patent application Pub. No. 2013/0267957 that are intended for single use have been developed. After such use, the cutting tool is simply discarded.

Single use cutting tools, however, typically lack structural rigidity which may adversely affect patient outcomes. Such structural rigidity minimizes unintended deflection of the cutting edge of the cutting tool that might result in an undesirable patient outcome. Deflection of a portion of the cutting tool, in particular deflection of a cutting edge against the surface of a bone during use could result in an inaccurate cut or deformed bone surface that is not desired. The cutting tool of Stamp, for example, requires the use of an additional support substrate that is used to structurally reinforce the cutting tool and minimize blade deflection.

The bone cutter of the present invention, unlike Stamp, is specifically designed to increase structural rigidity while minimizing the amount of material needed to construct the tool. Thus, improved rigidity while minimizing the amount of material used to construct the reamer provides a minimally invasive cutting tool that is more accurate during use; the unique structural design of the present cutting tool minimizes structural distortion under a mechanical load. Furthermore, by minimizing the amount of material required to construct the tool, the bone cutter of the present invention is more cost effective and easier to manufacture.

Therefore, what is needed is a low cost bone cutter that is easier to manufacture while providing improved structural rigidity.

Still further, what is needed is a method of manufacturing a cost effective bone cutter that provides at least a partial hemispherical form and where the cutter is not as susceptible to mechanical deflection as reamers of the prior art to consequently ensure accurate cutting.

SUMMARY OF THE INVENTION

A bone cutter designed to form at least a partial hemispherically shaped concave cavity in a bone, particularly for use to facilitate the implantation of a prosthetic cup during a hip replacement surgical procedure, is provided. The bone cutter of the present invention comprises a plurality of spaced apart struts that longitudinally extend from an apex to a base. Each of the struts comprise a plurality of cutting teeth having a cutting edge that is raised above the strut exterior surface. The plurality of struts radiating from the apex to the base thereby forms a bone cutter having a structure that is at least partially hemispherical. In addition, each of the struts comprise curved sides that increases the structural rigidity of the bone cutter. In an alternate embodiment, the bone cutter of the present invention may comprise a plurality of shields that are positioned between the struts. These shields further increase the structural rigidity of the bone cutter and help collect cutting debris therewithin.

The reamer is formed from a prefabricated substrate which is then pressed into a bone cutter having a body in the form of at least a partial hemisphere. Prior to press-forming, the flat metal body is stamped out of flat metal stock, optionally having a plurality of struts radiating from a center region. Perforations formed through the thickness of the struts of the substrate serve as tissue cutting apertures when the substrate is later formed into a hemispherical shape.

DETAILED DESCRIPTION OF THE PREFERRED EMBODIMENT

Figure 1:
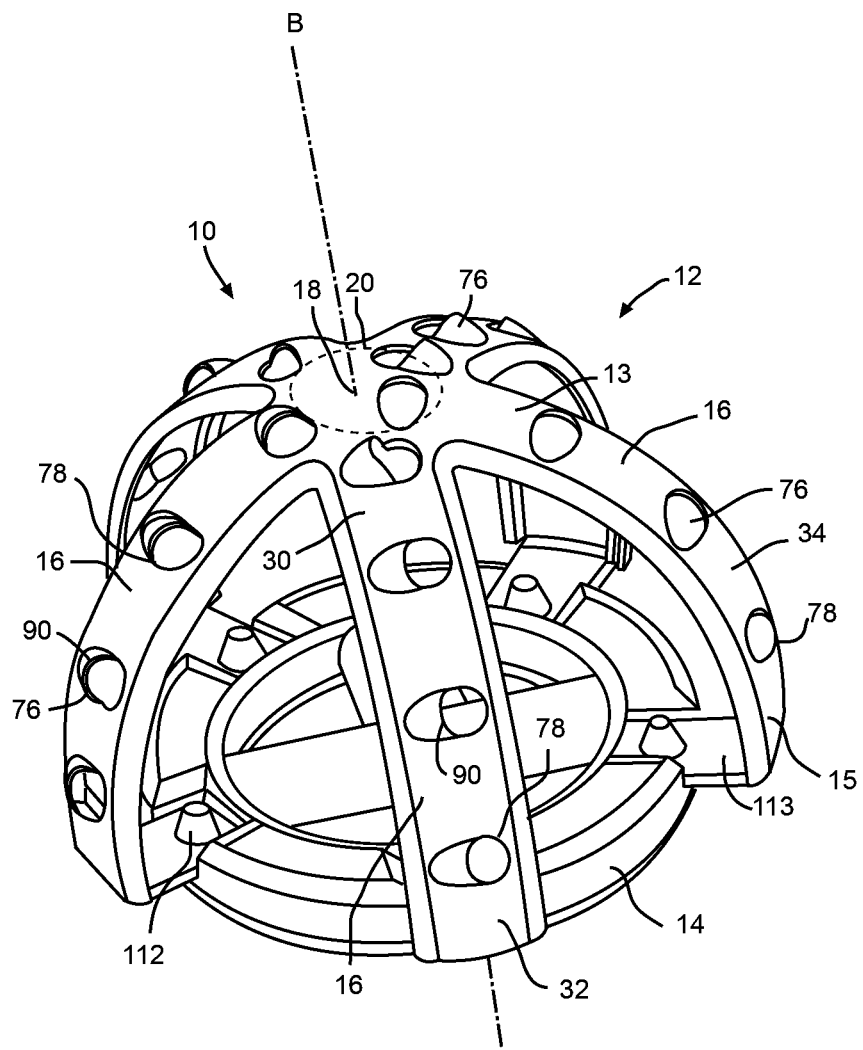
FIG. 1 is a perspective view of an embodiment of a bone cutter of the present invention.
Figure 2:
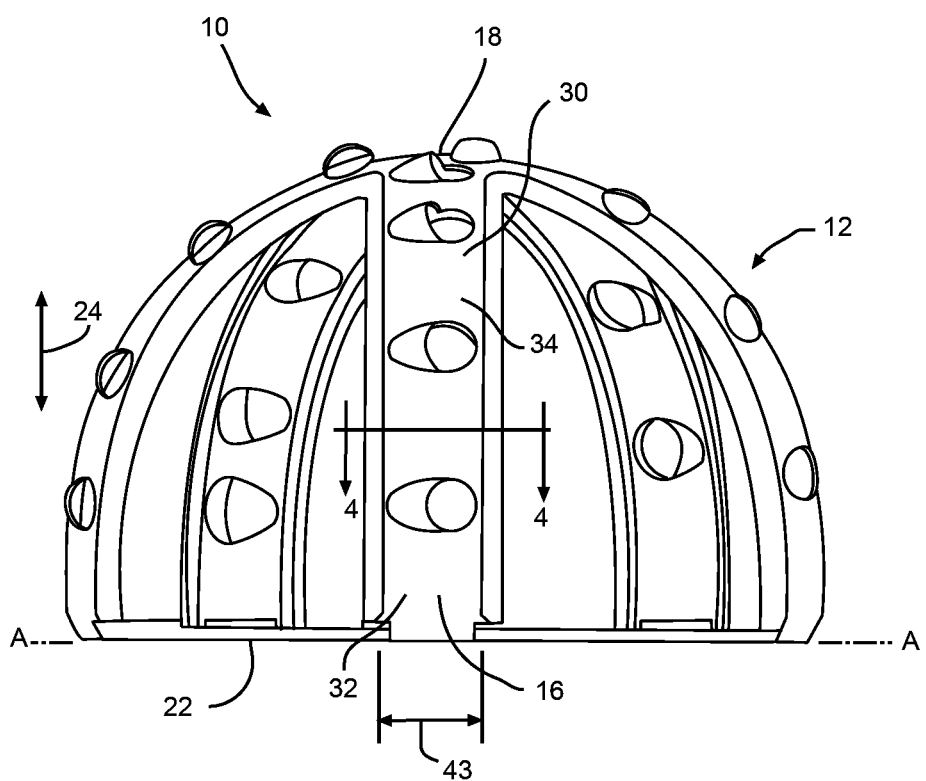
FIG. 2 illustrates a side view of the embodiment of the bone cutter illustrated in FIG. 1.

Now turning to the figures, FIGS. 1 and 2, illustrate a preferred embodiment of a bone cutter 10 of the present invention. As illustrated, the bone cutter 10 preferably comprises a bone cutter frame 12 connected to a bone cutter base 14. The frame 12 preferably comprises a plurality of spaced apart struts 16 that radially extend from a bone cutter apex 18, located at a bone cutter distal end 13, to the bone cutter base 14 located at an imaginary equatorial base plane A-A (FIG. 2) at a bone cutter proximal end 15. A rotational axis B-B extends through the apex 18.

Figure 3:
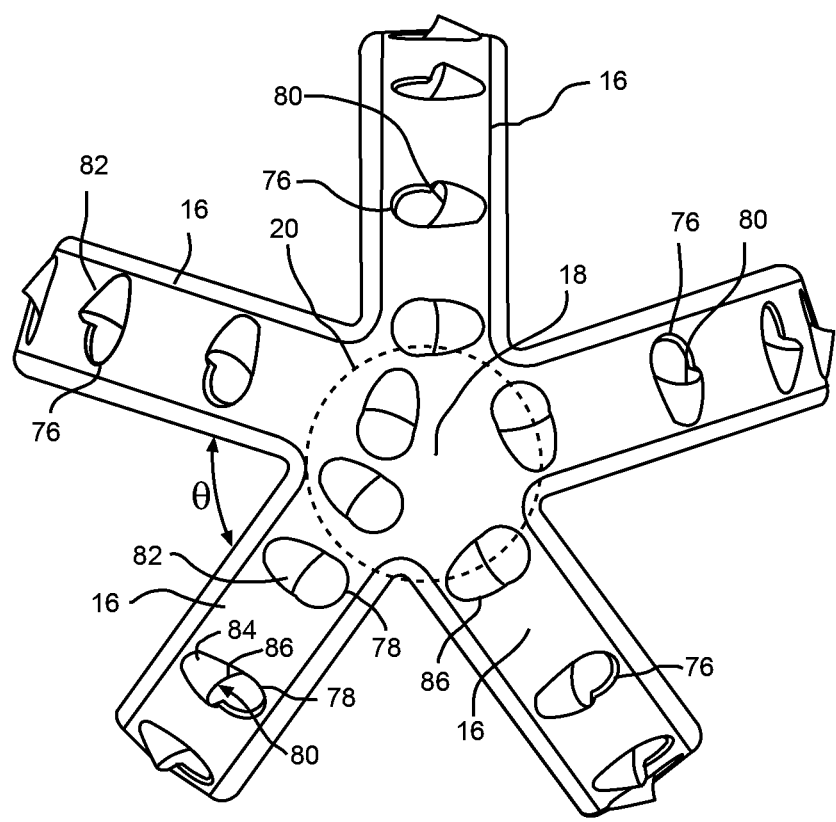
FIG. 3 shows a top view of the embodiment of the bone cutter frame illustrated in FIG. 1.

As shown in FIGS. 1, 2 and 3, each of the plurality of struts 16 preferably curves outwardly from the apex 18 such that they form the bone cutter frame 12 having at least a partial hemispherical shape. Thus, when the bone cutter 10 of the present invention is rotated about its rotational axis B-B against a bone surface, a concave cavity is formed therewithin. In the embodiment shown, five struts 16 are illustrated extending from the apex 18. However, it is contemplated that an additional or a fewer number of struts 16 may be utilized to form the bone cutter 10.

In a preferred embodiment, the base 14 defines an annular bone cutter outer perimeter at a lower base edge 22 of the cutter 10 (FIG. 2) having a diameter 21 (FIG. 10) ranging from about 20 mm to about 80 mm. In a preferred embodiment, the diameter of the base 14 that extends across the outer base perimeter is greater than a diameter of a central apex region 20 that annularly surrounds the apex 18. The bone cutter 10 also has a height 24 that extends from the lower base edge 22 to the apex 18 (FIG. 2). It is preferred that the bone cutter height 24 may range from about 10 mm to about 50 mm.

Furthermore, the base 14 provides strength and rigidity to the bone cutter 10. In addition, the base 14 provides a means for connecting a drive shaft 26 (FIG. 15) of a reamer spindle to the bone cutter 10. Thus, when the bone cutter 10 is connected to the drive shaft 26 a physician can operate the bone cutter 10 from a distal location. The bone cutter 10 can either be manually operated or, alternatively, be connected to a motor (not shown) to provide power assisted tissue removal.

Each of the plurality of struts 16 comprises an elongated length 28 (FIG. 12) that extends longitudinally between a distal strut end 30 and a proximal strut end 32. In a preferred embodiment, each of the distal strut ends 30 extends radially from the apex 18 while each of the proximal strut ends 32 extends towards the base 14 located at the equatorial base plane A-A. In addition, each of the struts 16 preferably comprises a strut sidewall 34 having a strut thickness 36 that extends perpendicular to the strut length 28 (FIG. 4).

As illustrated in FIGS. 1, 2, 3, 4, 7, 13, and 14 each of the plurality of struts 16 is preferably constructed having a cross-sectional shape oriented perpendicular to the strut length 28 similar to the shape of the letter "C". As will be discussed in more detail, this preferred construction of the struts 16 provides the bone cutter 10 of the present invention with increased mechanical strength and rigidity that results in a more precise cut.

Figure 4:
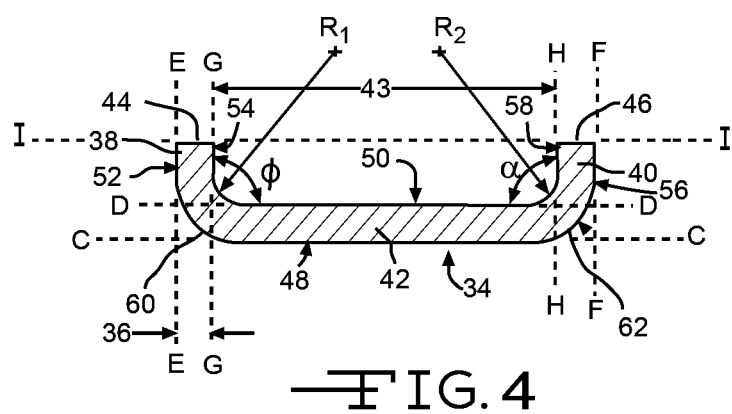
FIG. 4 is a magnified cross-sectional view perpendicular to the length of a strut of the bone cutter of the present invention.

FIG. 4 illustrates a magnified cross-sectional view of a strut 16 taken perpendicular to its length. In a preferred embodiment, each of the struts 16 comprises respective left and right secondary sidewall portions 38, 40 that extend from respective opposite sides of a primary sidewall portion 42. More specifically, each of the respective left and right secondary sidewall portions 38, 40 extend from opposite sides of a width 43 of the primary sidewall portion 42. As shown, the left secondary sidewall portion 38 having a left secondary sidewall portion end 44 extends from one side of the primary sidewall portion width 43. The right secondary sidewall portion 40 having a right secondary sidewall portion end 46 extends from the other, opposite side of the primary sidewall portion width 43. The respective ends 44, 46 of the left and right secondary sidewall portions 38, 40 preferably extend parallel to the width 43 of the primary sidewall portion 42.

The primary sidewall portion 42 has a primary portion exterior sidewall surface 48 that is opposed from a primary portion interior sidewall surface 50. As illustrated in FIG. 4, imaginary line C-C extends along the primary sidewall portion exterior surface 48 and imaginary line D-D extends along the primary portion interior surface 50. As illustrated in FIGS. 1, 2, 3, 7, 13, and 14, in a preferred embodiment, each of the struts 16 is positioned such that the interior surface 50 of the primary sidewall portion 42 faces towards the rotational axis B-B and the primary exterior surface 48 faces away from the rotational axis B-B.

Furthermore, the left secondary sidewall portion 38 comprises a left secondary sidewall exterior surface 52 opposed from a left secondary sidewall interior surface 54. Likewise, the right secondary sidewall 40 comprises a right secondary sidewall exterior surface 56 that is opposed from a right secondary sidewall interior surface 58. As illustrated in FIG. 4, imaginary line E-E extends along the exterior surface 52 of the left sidewall portion 38 and imaginary line F-F extends along the exterior surface 56 of the right sidewall portion 40. Imaginary line G-G extends along the interior surface 54 of the left sidewall portion 38 and imaginary line H-H extends along the interior surface 58 of the right secondary sidewall portion 40.

In addition, as illustrated in FIG. 4, a first intermediate sidewall portion 60 joins the left secondary sidewall portion 38 to the primary sidewall portion 42 and a second intermediate sidewall portion 62 joins the right secondary sidewall portion 40 to the primary sidewall portion 42. Both the first and second intermediate sidewall portions 60, 62 are preferably constructed having a curved orientation with respect to imaginary line D-D that extends along the interior surface 50 of the primary sidewall portion 42.

In a preferred embodiment, each of the struts 16 is constructed such that the exterior surfaces 52, 56 of the respective left and right secondary sidewall portions 38, 40, i.e., imaginary lines E-E and F-F are parallel to each other. Furthermore, each of the struts 16 may be constructed such that imaginary line C-C that extends along the exterior surface 48 of the primary sidewall portion 42 is oriented perpendicular to either of imaginary lines E-E or F-F. In other words, each of the struts 16 may be constructed such that the exterior surface 48 of the primary sidewall portion 42 is oriented perpendicular to either of the exterior surfaces 52, 56 of respective left and right secondary sidewall portions 38, 40.

Additionally, as illustrated in FIG. 4, the struts 16 may be constructed such that respective left and right ends 44 and 46 are oriented parallel to either imaginary lines C-C or D-D. As shown, imaginary line I-I extends along the exterior surfaces of left and right secondary sidewall ends 44 and 46. In a preferred embodiment, imaginary line I-I extends parallel to the surfaces of left and right sidewall ends 44, 46 such that respective left and right secondary sidewall portions 38, 40 are of about the same length. Furthermore, imaginary line I-I may extend parallel to either imaginary lines C-C or D-D. In addition, imaginary line I-I may extend about perpendicular to imaginary lines E-E and/or F-F.

In a preferred embodiment, the first intermediate sidewall portion 60, which joins the left secondary sidewall portion 38 to the primary sidewall portion 42, is preferably oriented at a first sidewall bend angle $\phi$. The second intermediate sidewall portion 62, which joins the right secondary sidewall portion 40 to the primary sidewall portion 42, is preferably oriented at a second sidewall bend angle $\alpha$. As defined herein, the first sidewall bend angle $\phi$ is the angle between imaginary line D-D that extends along the interior surface 50 of the primary sidewall portion 42 and imaginary line G-G which extends along the interior surface 54 of the left sidewall portion 38. The second sidewall bend angle $\alpha$ is the angle between imaginary line D-D that extends along the interior surface 50 of the primary sidewall portion 42 and the imaginary line H-H that extends along the interior surface 58 of the right sidewall portion 40. In a preferred embodiment either of the first or second sidewall bend angles $\phi$, $\alpha$ may range from about 45° to about 160°. More preferably, either of the first and second sidewall bend angles $\phi$, $\alpha$ may range from about 75° to about 135°. Most preferably, either of the first and second sidewall bend angles $\phi$, $\alpha$ is about 90°.

In addition, as illustrated in FIG. 4, each of the struts 16 may be constructed such that the first intermediate sidewall portion 60 has a first radius of curvature $R_1$ and the second intermediate sidewall portion is constructed having a second radius of curvature $R_2$. As defined herein, the first radius of curvature $R_1$ is the curvature of the interior surface of the first intermediate sidewall portion 60 as it transitions from the interior surface 50 of the primary sidewall portion 42 to the interior surface 54 of the left sidewall portion 38. The second radius of curvature $R_2$ is the curvature of the interior surface of the second intermediate sidewall portion 62 as it transitions from the interior surface 50 of the primary sidewall portion 42 to the interior surface 58 of the right sidewall portion 40. In a preferred embodiment, either of the first or second radius of curvatures $R_1$, $R_2$ may range from about 0.25 to 3 times the sidewall thickness 36 or, alternatively, they may range from about 0.25 mm to about 2 mm.

As shown in FIG. 3 each of the plurality of struts 16 is positioned at an offset angle $\theta$ from each other. In a preferred embodiment, the offset angle $\theta$ may range from about 40° to about 120°. The offset angle $\theta$ is the angle between external surfaces of respective adjacent left and right secondary sidewall portions. In a preferred embodiment, the offset angle $\theta$ is established by positioning the plurality of struts radiating equally from the apex 18. In this embodiment, the offset angle would be determined by diving 360° by the number of struts. For example, if the bone cutter 10 is constructed with four struts, and assuming the primary sidewall width 43 is negligible, the offset angle would be about 90°. In practice, the width 43 is not negligible so the offset angle between adjacent struts in a four strut bone cutter is less than 90°. Similarly, if the bone cutter 10 is designed with five struts, the offset angle $\theta$ would be some angle less than 72° taking into account the primary sidewall width 43. This offset angle $\theta$ provides additional rigidity to the bone cutter 10 and ensures a smooth concave cut surface.

As previously mentioned, Stamp in U.S. patent application publication number 2013/0267957 discloses an orthopedic cutting tool that is constructed from a metallic "planar shim" having extending limbs. However, unlike the bone cutter 10 of the present invention, the cutting tool of Stamp lacks the curved orientation of the left and right sidewall portions with respect to the primary sidewall portion 42 as previously discussed.

Figure 5:
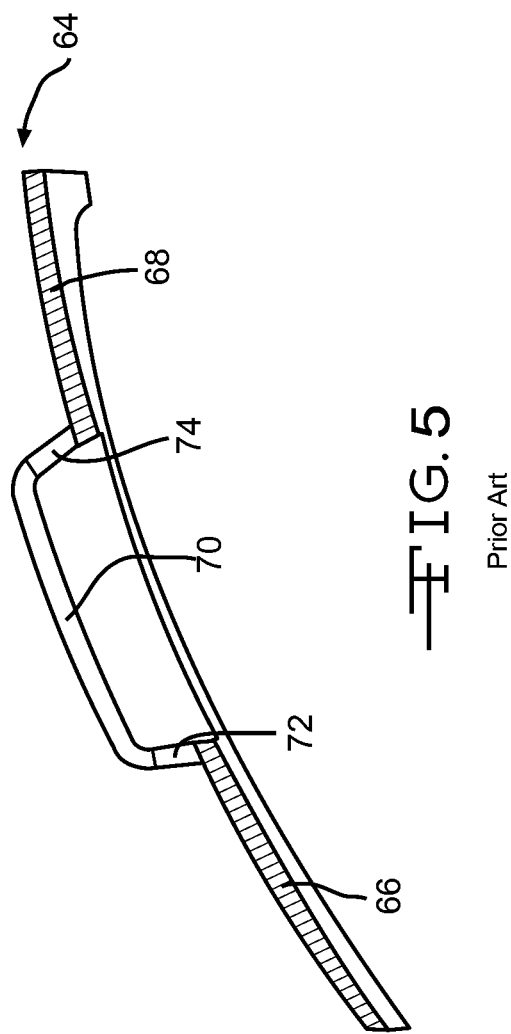
FIG. 5 is a cross sectional view of an prior art embodiment.

FIG. 5 illustrates a modified cross-sectional view of an embodiment of a limb 64 of the Stamp cutting tool. Specifically, FIG. 5 shows a cross-sectional view of a Stamp limb 64 taken from FIG. 6 of the '957 publication with the mold tool 40 removed. As illustrated, the cutting tool limb 64, unlike the strut 16 of the cutting tool 10 of the present invention, is constructed having left and right flanges 66, 68 that extend about parallel from opposing sides of a cutting surface 70 having a planar surface. In addition, the Stamp embodiment comprises respective left and right transition portions 72, 74 that connect the cutting surface 70 to the left and right flanges 66, 68. These distinct structural differences between Stamp and the struts 16 of the cutting tool 10 of the present invention significantly affects the structural rigidity of the respective cutting tools. In the case of the cutting tool 10 of the present invention, the angular orientation of the left and right secondary sidewall portions 38, 40, particularly with the addition of the first and second transition portions 60, 62, provides a cutting tool 10 having an increased area moment of inertia of its cross-sectional shape while using a lesser amount of material. This translates into minimized deflection of the cutting surface thus providing a more precise cut over prior cutting tools such as Stamp.

Figure 6:
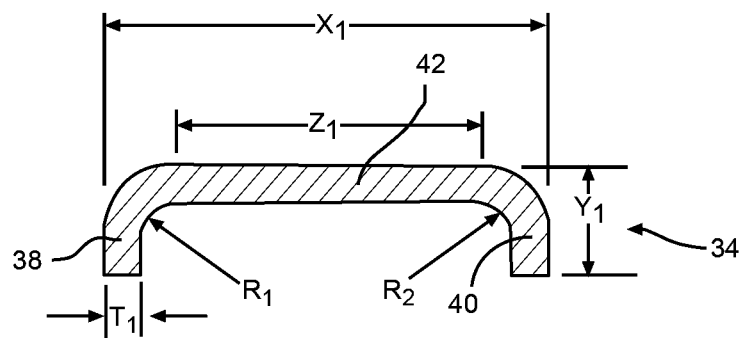
FIG. 6 is a cross-sectional view of the strut of the bone cutter of the present invention taken perpendicular to its length.
Figure 6A:
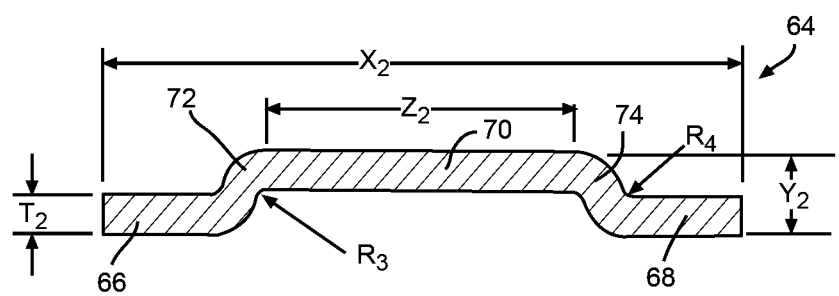
FIG. 6A illustrates a cross-sectional view of a limb of a prior art bone cutter taken perpendicular to its length.
Figure 7:
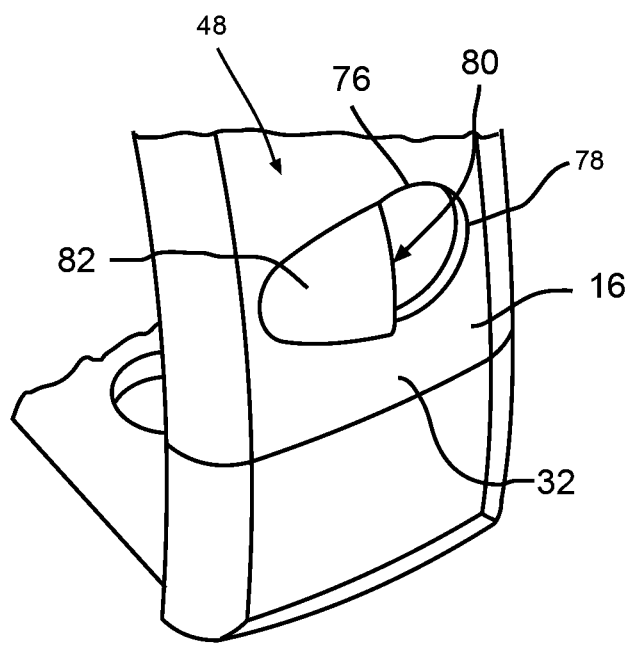
FIG. 7 illustrates a magnified perspective view of a cutting tooth utilized by the bone cutter shown in FIG. 1.

FIGS. 6 and 6A illustrate a comparative example between a strut 16 of the bone cutter 10 of the present invention (FIG. 6) to a limb 64 of a bone cutter of Stamp. Specifically, FIG. 6 is a cross-sectional view of a strut 16 of the bone cutter 10 of the present invention that is similar to FIG. 4. FIG. 6A illustrates a comparative cross-section of a limb 64 of Stamp adapted from the cross-sectional view of FIG. 6 in the '957 publication. In the comparative example provided in respective FIGS. 6 and 6A, it was assumed that both the limb 64 of Stamp and the strut 16 of the present invention are composed of the same metal. In addition, it was assumed that both the limb 64 of Stamp and the strut 16 of the present invention have the same metal thickness, (about 1 mm), $T_1$ for the strut 16 and $T_2$ for the limb of Stamp. Furthermore, in the comparative model, it was assumed that the span of the primary sidewall portion 42, "$Z_1$" of the strut 16 and the cutting edge portion 70, "$Z_2$" of the limb 64, are about the same length, about 7.75 mm. However, unlike the present invention, the limb 64 of Stamp comprises respective left and right flanges 66, 68 that extend outwardly and in parallel to the cutting portion 70. Thus, because Stamp comprises respective left and right flanges, 66, 68 that extend about parallel to the cutting surface 70, the radius of curvatures of the first and second transition portions of Stamp, $R_3$ and $R_4$ where calculated to be less than the radius of curvature between the primary sidewall portion 42 and respective left and right sidewall portions 38, 40. For example, radius of curvatures R₁ and R2 formed between the primary 42 and respective right and left sidewall portions 38, 40 were assumed to have a radius of curvature of about 0.75. In contrast, because of the abrupt transition between the respective right and left flanges 66, 68, caused by the parallel orientation of the flanges to the cutting surface 70, respective radius of curvatures $R_3$ and $R_4$ were assumed to be about 0.25. Furthermore, it was assumed that the respective left and right flanges 66, 68 of the Stamp limb 64 would proportionally extend further than the total cross-sectional span of the strut cross-section of the present invention.

Assuming the relative constructions of the limb 64 of Stamp and the strut 16 of the present invention are similar to a beam, a mathematical estimation of the area moment of inertia between the two embodiments was made. As defined herein, "area moment of inertia" is a property of a two-dimensional plane shape which characterizes its deflection under a load. Thus, the greater the value of the moment of inertia, the more resistant the shape is to deflection. As related to the bone cutter of the present invention, an increased area moment of inertia would indicate that the structure is less susceptible to bend under a load and therefore is more rigid. Assuming the structure of Stamp as disclosed and illustrated in FIG. 6A and the construction of a strut of the bone cutter of the present invention, a mathematical model of the area moment of inertia of the two distinctly different structures was created using the following equations:

$$\delta \alpha \frac{1}{I_{xx}} \qquad \text{Equation 1}$$

$$I_{xx} = \int y^2 dx dy \qquad \text{Equation 2}$$

where $I_{xx}$ is the area moment of inertia, δ is the deflection of a beam, y is the cross-sectional height of the simulated beam and x is the cross-section width of the simulated beam.

As illustrated in FIGS. 6 and 6A, $y_1$ designates the cross-sectional height for the strut of the present invention and $y_2$ designates the cross-sectional height for the limb of Stamp. In addition, $x_1$ designates the cross-section width for the strut of the present invention and $x_2$ designates the cross-section width of the limb 64 of Stamp. For the comparative model, it was assumed that $y_1$ was 11.25 mm, $x_1$ was 2.75 mm, $y_2$ was 16 mm and $x_2$ was 2.25 mm. Thus, using equations 1 and 2 above and assuming the comparative dimensions as previously described and shown in FIGS. 6 and 6A, the area moment of inertia values of the two structures were calculated and are shown in Table I below.

TABLE I

|  | Stamp Embodiment | Present Invention |
|---|---|---|
| Area Moment of Inertia | 6.23 | 6.49 |
| Cross Sectional Area | 17.05 | 13.68 |

Table 1 depicts the area moment of inertia of the strut of the present invention compared to the limb of Stamp. As shown, the area moment of inertia of the strut 16 of the present invention was calculated to be greater than the limb 64 of Stamp. Furthermore, the cross-sectional area taken perpendicular to the lengths of the respective strut of the present invention and the limb of Stamp was calculated to be greater for the shim of Stamp. This indicates that the strut of the present invention is not only more resistant to deflection than the shim of Stamp, but is also of a more efficient design than Stamp as the strut of the present invention comprises a smaller cross-sectional area. Furthermore, the mathematical simulation above indicates that the structure of the struts of the present invention having curved side widths provides the bone cutter with a greater structural integrity.

As illustrated in FIGS. 1, 2, 3, 7, 13, and 14, each of the plurality of struts 16 comprises a plurality of cutting teeth 76 that extend outwardly from the exterior strut sidewall surface. More preferably, each of the plurality of cutting teeth 76 extends outwardly from the exterior surface 48 of the primary strut sidewall portion 42. In a preferred embodiment the plurality of cutting teeth 76 are positioned spaced apart from each other and reside along the length 28 of each of the struts 16. Each of the cutting teeth 76 comprises a cutting tooth aperture 78 that extends through the strut thickness 36 of the primary sidewall portion 42. In a preferred embodiment, each cutting aperture 78 may be constructed having a shape that is similar to the letter "D" or "C". Each aperture 78 is dimensioned suitable for passing debris into an interior region of the bone cutter frame 12 where the debris may accumulate.

Figure 8:
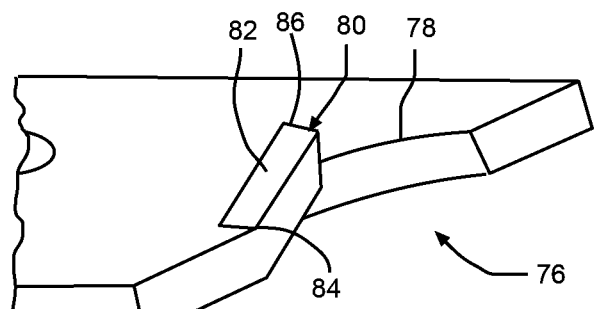
FIG. 8 is a magnified cross-sectional view of the cutting tooth of the bone cutter of FIG. 1.

Furthermore, as illustrated in FIG. 8, each of the cutting teeth 76 comprises a tissue cutting surface 80 that at least partially extends about the perimeter of the aperture 78. More specifically, the tissue cutting surface 80 preferably resides above the cutting tooth aperture 78. Each of the plurality of cutting teeth 76 preferably comprises a raised portion 82 that is integrated with the body of the strut 16. In a preferred embodiment, the raised portion comprises a first end 84 that extends to a second end 86 having the tissue cutting surface 80. The first end 84 is preferably an extension of the exterior strut surface and the tissue cutting surface 80 is an extension of the raised portion extending to the second end 86 positioned spaced above the cutting tooth aperture 78. In other words, the raised structure 82 preferably comprises a partial dome structure having a partial dome base 88 that extends to a cutting dome apex 90 (FIG. 1) residing over the cutting tooth aperture. The dome base 88 is defined by at least a portion of the perimeter of the strut 16 surrounding the cutting tooth aperture 78. In preferred embodiment, the thickness of the cutting dome shell forms the thickness of the tissue cutting surface 80 of the tooth 76.

As illustrated in FIGS. 1, 2, 3, 7, 13, and 14 each of the cutting surfaces 80 of the cutting teeth 76 is preferably positioned facing the direction of cut. It is further preferred that each of the cutting surfaces 80 of the cutting teeth 76 lie within an imaginary plane J-J (FIG. 9) extending into and out of the paper that intersects the rotating axis A-A. More specifically, each of the plurality of teeth 76 is positioned about the strut 16 of the bone cutter 10 such that an imaginary point 92 (FIG. 12) positioned in the middle of the tooth cutting surface 80, i.e., at the cutting raised dome apex 90, lies within an imaginary plane that intersects the rotational axis B-B.

Figure 12:
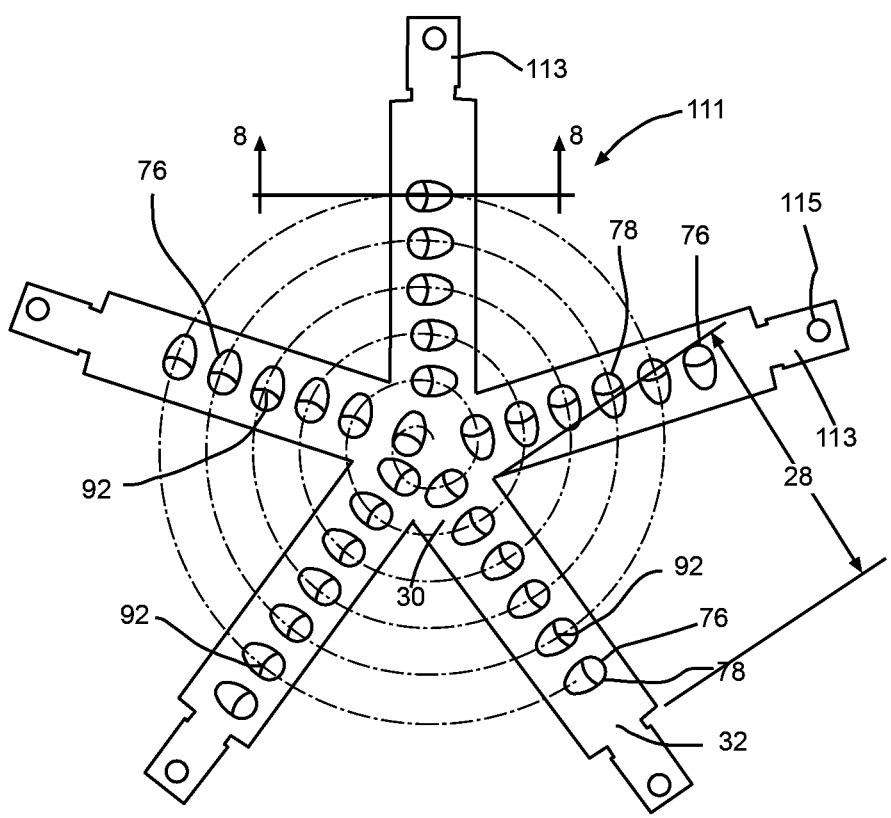
FIG. 12 shows an embodiment of a flat metal stock bone cutter pre-form prior to stamping into the preferred frame structure of the bone cutter of the present invention.

In addition, as illustrated in FIG. 12, it is preferred that the plurality of cutting teeth 76 is arranged in a spiral pattern about the exterior surface of the bone cutter 10. As illustrated in FIG. 12, each of the imaginary points 92 that centrally lie on the cutting surface 80 is positioned in a spiral pattern that originates from the apex 18 and extends outwardly and towards the proximal strut end 30. This is to ensure that as the bone cutter 10 is rotated, each of the cutting teeth 76 encompasses a portion of the cavity being cut.

Figure 9:
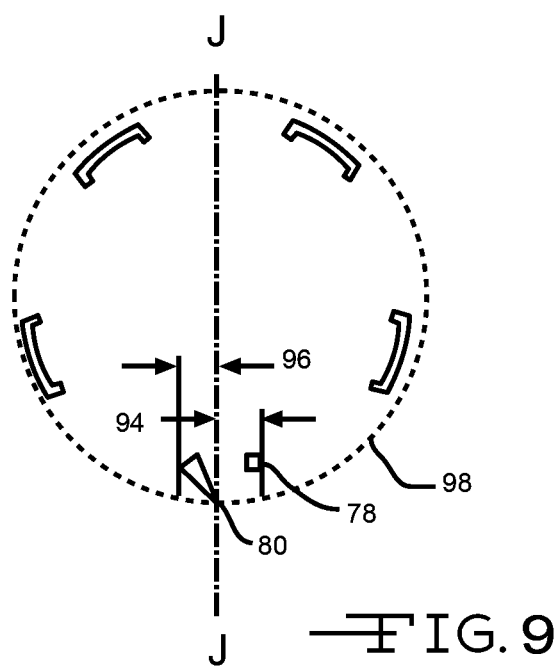
FIG. 9 illustrates a cross-sectional view of a preferred position of the cutting tooth of the present invention.

As illustrated in FIGS. 1, 2, 3, 9, 13, and 14, each of the cutting teeth 76 resides within the primary portion 42 of the strut 16 such that a margin of material surrounds each tooth 76. In a preferred embodiment, as shown in FIG. 9, a leading material margin 94 that resides in front of the cutting surface 80 is greater than a trailing material margin 96 that resides in behind the cutting surface 80. The leading material margin 94 is defined as the length of material that extends from the cutting surface 80 of the cutting tooth 76 to the exterior surface 56 of the right secondary portion sidewall 40. The trailing material margin 96 is defined as the length of the portion of the strut that extends from the cutting surface 80 of the cutting tooth 76 to the exterior surface 52 of the left secondary portion sidewall 38. This preferred structure for the cutting surfaces 80 ensures an even cut along the cutting plane 98.

Figure 10:
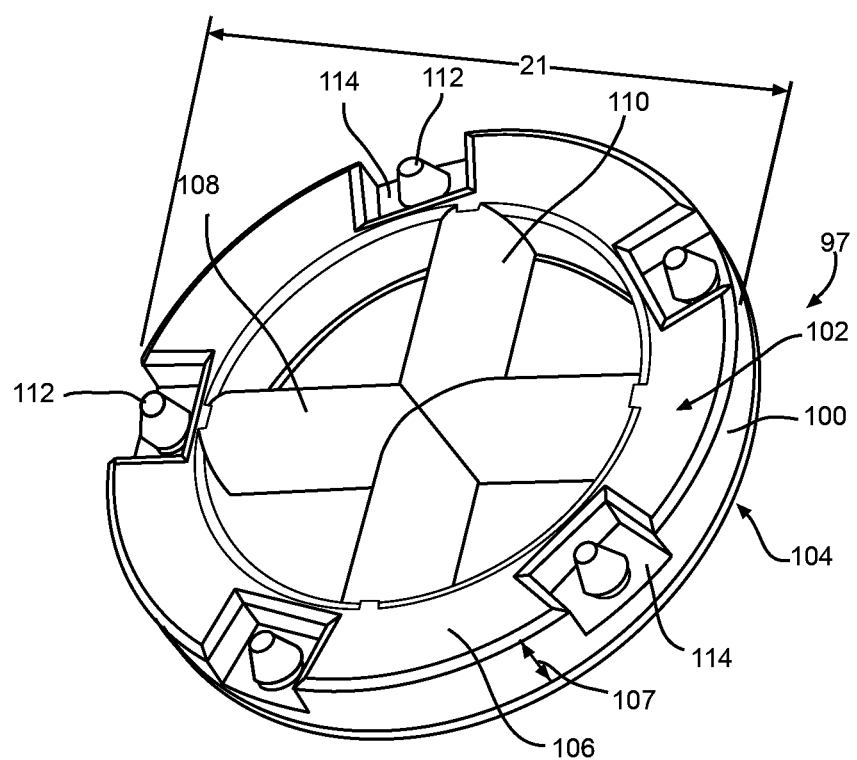
FIG. 10 illustrates an embodiment of a base comprising a cross-bar driver engagement interface that may be used with the bone cutter shown in FIG. 1.
Figure 10A:
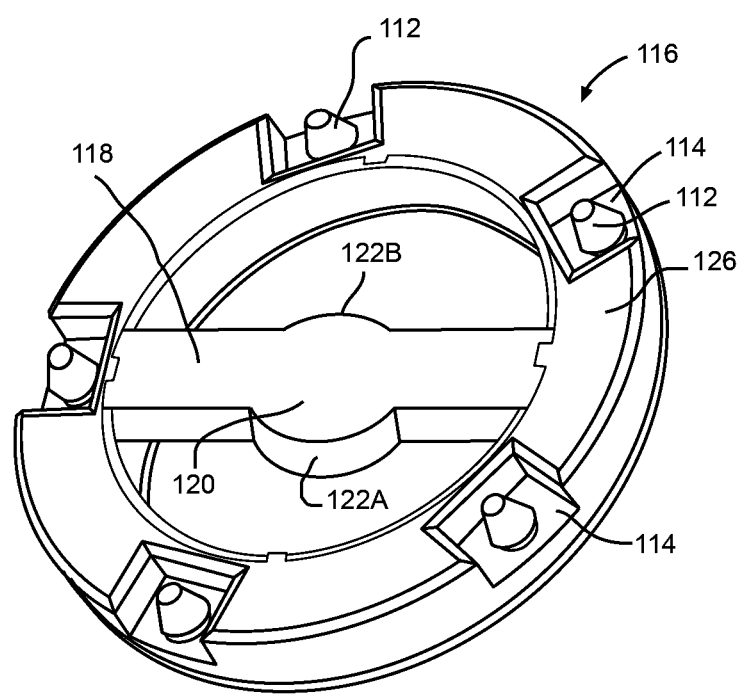
FIG. 10A illustrates an alternate embodiment of a base comprising a bar and boss driver engagement interface that may be used with the bone cutter shown in FIG. 1.

FIGS. 10 and 10A illustrate different embodiments of the base 14 that may be utilized with the bone cutter of the present invention. The base 14 is designed to enable engagement of the bone cutter 10 with a shaft 26 or driver. FIG. 10 illustrates a preferred embodiment of a base 14 of the invention having a cross-bar interface 97. As shown, the base 14 comprises a base sidewall 100 having opposing upper and lower base surfaces 102, 104. In a preferred embodiment, the base 14 may comprise a perimeter ring 106 having a perimeter thickness 107 defined by the upper and lower surfaces 102, 104 that annularly extends about the perimeter of the bottom of the bone cutter 10. First and second cross bars 108, 110 preferably intersect within the perimeter ring 106, thus forming the cross bar drive interface 97. In a preferred embodiment, the lower surface 104 of the base 14 is planar.

FIG. 10A illustrates an alternative embodiment of the base 14 having a bar and boss drive interface 116. As shown, the driver interface 116 comprises a bar and boss having a bar portion 118 that extends to a boss 120. The boss 120 has opposed semi-circular sides 122A, 122B meeting the bar portion 118. Similar to the previous embodiment of the base 14 having the cross bar drive interface 98, the bar and boss interface 116 also comprises a base sidewall 126 that surrounds the bar and boss interface 116.

Both base sidewalls 100, 126 of the cross-bar and bar and boss interfaces 97, 116 provides a preferred means of attaching the frame 12 of the bone cutter 10 to the base 14. As illustrated in FIGS. 10 and 10A, the frame is preferably attached to anchor posts 112 that reside within receiving recesses 114. The anchor posts 112 are projections that extend upwardly within the receiving recesses 114. In a preferred embodiment the anchor posts 112 are received within holes 115 (FIG. 12) that extend through a thickness of tab portions 113 that reside at the strut proximal ends 32.

In a preferred embodiment, either embodiment 97, 116 of the base 14 can be attached to the frame 12 by a base fastener (not shown) such as a rivet, bolt, or screw. Alternatively, the base 14 may be attached to the cutter frame 12 by means of a snap fit connection, or weld connection such as a laser weld, resistance weld or ultrasonic weld connection. In a preferred embodiment illustrated in FIGS. 1, 7 and 12, a tab 113 extending from the proximal end 32 of at least one strut 16 may be used to secure the frame 12 to the base 14. As shown, tab 113 is preferably snap fitted over anchor posts 112 to provide the connection between the frame 12 and the base 14. Alternatively, a fastener (not shown) may be positioned through a tab hole 115 that extends through the thickness of the tab 113 to form a more secure connection of the base 14 to the bone cutter frame 12.

Figure 11:
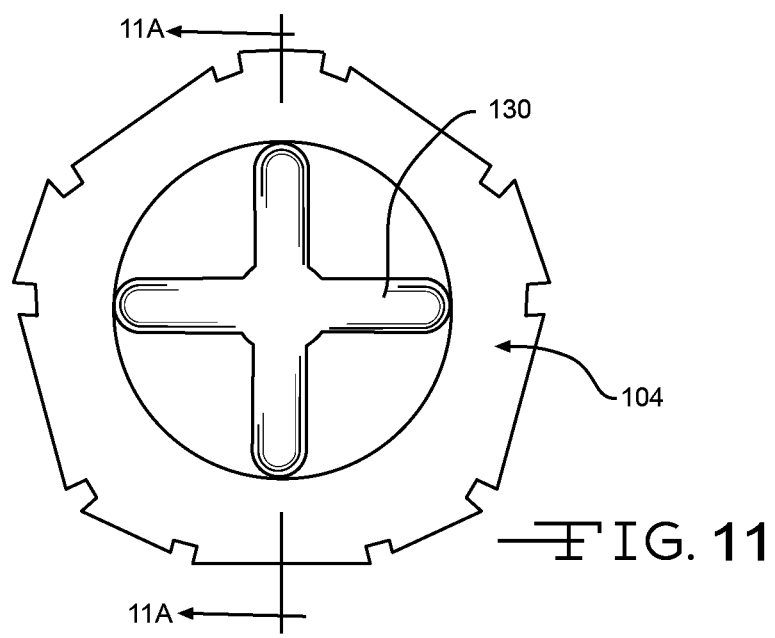
FIG. 11 illustrates an embodiment in which a polymeric overlay may be applied to the exterior surface of the base.
Figure 11A:
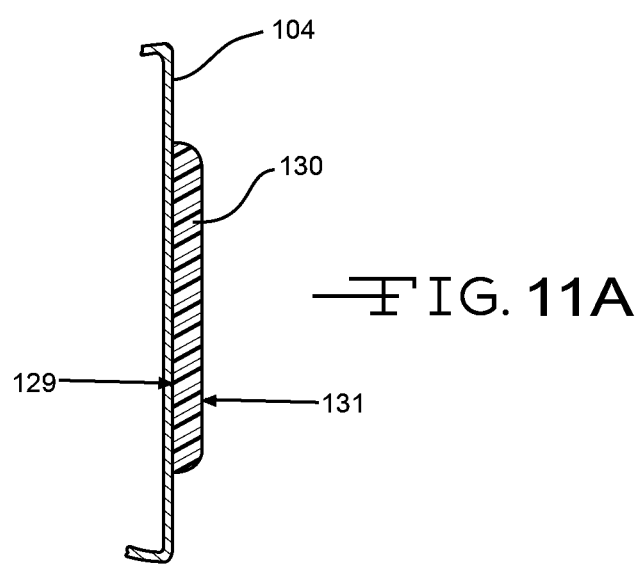
FIG. 11A illustrates a cross-sectional view of the embodiment shown in FIG. 11.

As illustrated in FIGS. 11 and 11A, a removable driver engagement overlay 130 may be applied to the bottom surface 104 of the base 14. The overlay 130 is designed to facilitate removable attachment of the bone cutter 10 to a driver shaft 26. In a preferred embodiment, the overlay 130 is applied to the planar bottom surface 104 of the base 14. More preferably, the overlay 130 is designed to be applied to the exterior surface of the intersecting first and second cross bars 108, 110 or bar and boss 118, 120 having a planar surface. The overlay 130 preferably comprises a first planar surface 129 that extends to a second surface 131 having a curved cross-section. In a preferred embodiment, the curved second surface of the base overlay 131 is designed to be received within a capture mechanism of the driver shaft 26. Thus, the curved cross-section shape of the overlay 130 provides a surface to which the capture mechanism of a reamer spindle can easily connect to. The base overlay 130 is preferably composed of a polymeric material such as acrylonitrile butadiene styrene, an acrylic polymer, nylon, and polyethylene. The overlay 130 is preferably attached to the bottom base surface 104 of the bone cutter 10 using a snap-fit construction or with an adhesive material.

In a preferred embodiment, the bone cutter 10 of the present invention is fabricated in a metal stamping process where a sheet of flat stock metal is first cut out in the general shape of the bone cutter frame 12. FIG. 12 illustrates an embodiment of a sheet of flat stock metal that has been cut in a pre-form shape 111 of the cutter frame 12. As illustrated, the pre-form shape 111 comprises a central region in which arms 119 of the pre-form shape 111 radially extend. The number of pre-form arms 119 equal the number of formed struts 16 in the fabricated cutter frame 12. Once the sheet of flat stock metal has been cut to the desired pre-form shape 111, the cutting teeth 76 are formed by a metal stamping process. In a preferred embodiment, the stamping process forms the cutting aperture 78 and bends a portion of the metal to form the raised 82 of the cutting tooth 76. In addition, the stamping process bends the elongated sides of the arms 119, thus forming the respective left and right secondary sidewall portions 38, 40.

Figure 13:
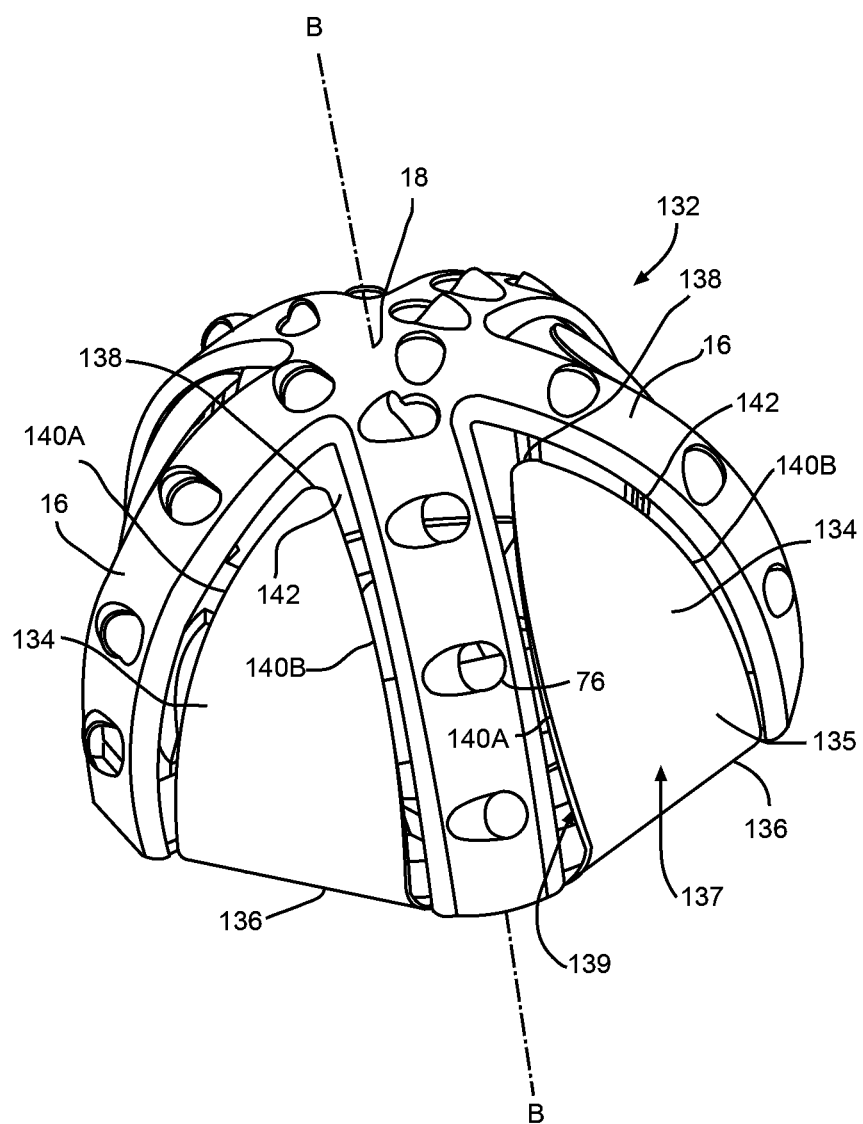
FIG. 13 is a perspective view of an alternate embodiment of a bone cutter of the present invention comprising a plurality of shields positioned between adjacent struts.
Figure 14:
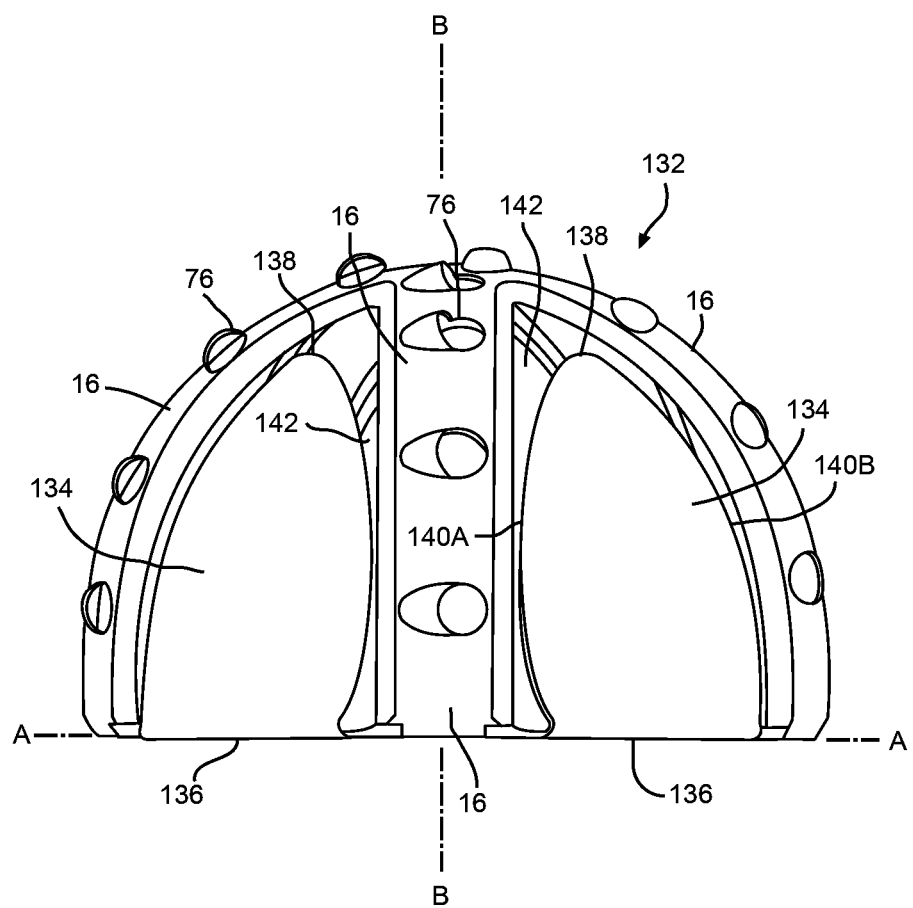
FIG. 14 is a side view of the alternate embodiment of the bone cutter illustrated in FIG. 13.

FIGS. 13 and 14 illustrate an alternate embodiment of a bone cutter 132 of the present invention. In the embodiment shown, the bone cutter 132 comprises a plurality of shields 134 that are each positioned between adjacent struts 16 of the bone cutter 132. In a preferred embodiment, each of the shields 134 comprises a shield sidewall 135 having a shield thickness that extends between opposing exterior and interior shields surfaces 137, 139. In addition, each of the shields 134 comprises an outer perimeter of a partial hemispherical shape. As illustrated, each of the shields 134 extends from the base 14 towards the bone cutter apex 18. Each shield 134 further comprises a shield base 136 that extends upwardly to a shield apex 138. In a preferred embodiment, the shield base 136 may be an integral part of the base 14. As shown, the shield base portion 136 is preferably oriented in a hinged relationship with the base 14. The respective first and second sides 140A, 140B of the shield 134 are curved such that they are able to be received between the struts 16 of the bone cutter 132. In a preferred embodiment, the shields 134 are formed to the curvature of the bone cutter 132 and are recessed from the exterior surface of the strut 16. Furthermore, it is preferred that a gap 142 extend between the respective first and second sides 140A, 140B of the shield 134 and the adjacent struts 16. In a preferred embodiment, the gap 142 may range from about 0.01 mm to about 10 mm. The gap 142 and recessed shield features of the bone cutter 132 are designed to minimize surface contact of the cutter 132 with the bone and/or tissue intended to be cut. Thus, these features increase the minimally invasive properties of the bone cutter 132.

Figure 15:
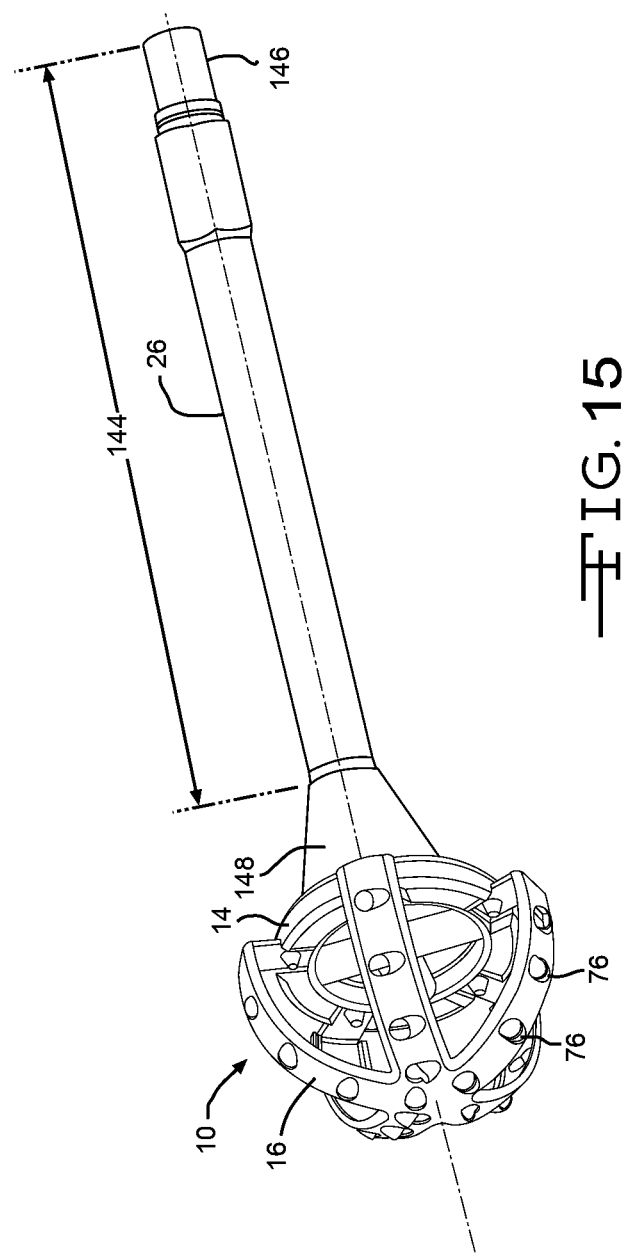
FIG. 15 shows an embodiment of the bone cutter of the present invention connected to a drive shaft.

FIG. 15 illustrates an embodiment of a drive shaft or spindle 26 that may be used to control and maneuver the bone cutter 10, 132. As shown, the drive shaft 26 comprises a drive shaft length 144 extending from a drive shaft proximal end 146 to a drive shaft distal end 148. In a preferred embodiment, the bone cutter 10, 132 may be detachably fastened to the drive shaft distal end 148 and the drive shaft proximal end 146 may be used as a handle or, alternatively, may be connected to a motorized mechanism (not shown). In a preferred embodiment, the base 14 of the bone cutter 10, 132 may be detachably fastened to the distal end 148 of the drive shaft 26. Alternatively, the frame 12 of the bone cutter 10, 132 may be directly connected to the drive shaft distal end 148 without the use of a base 14. A plurality of fasteners (not shown) may be used to connect the bone cutter 10, 132 to the drive shaft distal end 148.

While the preferred embodiments of the cutting device and methods have been described in reference to the environment in which they were developed, they are merely illustrative of the principles of the inventions. Other embodiments and configurations may be devised without departing from the spirit of the inventions and the scope of the appended claims.

What is claimed is:

1. A bone cutter, comprising:
   (a) a base residing along an equatorial base plane;
   (b) a cutting frame, comprising:
      (i) a frame apex and a plurality of struts, each strut having a longitudinal strut wall extending from the frame apex to a strut proximal end, wherein the strut proximal end is connected to the base, and
      (ii) wherein each of the plurality of struts has a horizontal cross-sectional profile defined by a primary sidewall portion and a first intermediate sidewall portion and left secondary sidewall portion wherein said first intermediate sidewall portion is oriented at a first sidewall bend angle $\Phi$ and a second intermediate sidewall portion which joins a right secondary sidewall portion to said primary sidewall portion; wherein said second intermediate sidewall portion is oriented at a second sidewall bend angle $\alpha$, wherein said first or second sidewall bend angles $\Phi$ or $\alpha$, respectively, range from 45° to 160°, and wherein said first intermediate sidewall portion has a first radius of curvature $R_1$ and the second intermediate sidewall portion has a radius of curvature $R_2$ range from 0.25 mm to 2.0 mm; and
   (c) a plurality of cutting teeth arrayed along at least one of the plurality of struts.

2. The bone cutter of claim 1, wherein the plurality of struts each curve in a partially hemispherical shape from the frame apex to the respective strut proximal end at the equatorial base plane.

3. The bone cutter of claim 1, wherein the cutting frame is composed of a polymeric material, a metal, a ceramic material, and combinations thereof.

4. The bone cutter of claim 1, wherein the longitudinal strut walls each have an exterior surface and an interior surface, the interior surface facing an imaginary rotational axis extending from the frame apex to the equatorial base plane, and wherein each of the exterior and interior surfaces possess a strut width, the strut width extending parallel to the equatorial base plane, and further wherein the strut width of the exterior surface of the longitudinal wall is concave with respect to the imaginary rotational axis, such that the exterior surface curves away from the imaginary rotational axis as the strut extends from the apex to the strut proximal end connected to the base.

5. The bone cutter of claim 1, wherein a cutting surface of each of the plurality of cutting teeth extends at least partially over an aperture extending through the longitudinal strut wall, respectively.

6. The bone cutter of claim 1, wherein the base of the bone cutter is configured for detachable connection to a drive shaft.

7. The bone cutter of claim 1, wherein the strut proximal end further comprises a tab, the tab residing along a plane parallel to the equatorial base plane, and wherein the tab extends from the strut proximal end to the base.

8. The bone cutter of claim 7, wherein a tab is connected to the base by an anchor post.

9. The bone cutter of claim 1, wherein the plurality of struts curve in a semi-hemispherical shape from the frame apex to the strut proximal end at the equatorial base plane.

10. The bone cutter of claim 1, wherein the semi-hemispherical frame is composed of a polymeric material, a metal, a ceramic material, and combinations thereof.

11. The bone cutter of claim 1 wherein said first or second sidewall bend angles $\Phi$ or $\alpha$, respectively, range from 75° to 135°.

12. The bone cutter of claim 1 wherein said first or second sidewall bend angles $\Phi$ or $\alpha$, respectively, is 90°.

13. The bone cutter of claim 1 wherein said plurality of struts comprises five struts.

14. The bone cutter of claim 1 wherein said plurality of struts include a major wall wherein a cutting surface of each of the plurality of cutting teeth extends at least partially over an aperture extending through a strut major wall.

15. The bone cutter of claim 1 wherein said plurality of struts are positioned at an offset angle $\theta$ that ranges from 40° to 120°.

* * * * *